United States Patent
Rowe

(10) Patent No.: US 10,144,980 B2
(45) Date of Patent: Dec. 4, 2018

(54) SOLID AGAVE SYRUP COMPOSITIONS

(71) Applicant: IAF SCIENCE HOLDINGS LTD., Hamilton (BM)

(72) Inventor: John Lawrence Rowe, Charlottetown (CA)

(73) Assignee: IAF SCIENCE HOLDINGS LTD., Hamilton (BM)

( * ) Notice: Subject to any disclaimer, the term of this patent is extended or adjusted under 35 U.S.C. 154(b) by 586 days.

(21) Appl. No.: 14/414,627

(22) PCT Filed: Jul. 11, 2013

(86) PCT No.: PCT/CA2013/050538
§ 371 (c)(1),
(2) Date: Jan. 13, 2015

(87) PCT Pub. No.: WO2014/008603
PCT Pub. Date: Jan. 16, 2014

(65) Prior Publication Data
US 2015/0126617 A1    May 7, 2015

Related U.S. Application Data

(60) Provisional application No. 61/671,159, filed on Jul. 13, 2012.

(51) Int. Cl.
| | | |
|---|---|---|
| A61K 36/00 | (2006.01) | |
| C13B 50/00 | (2011.01) | |
| A23L 5/00 | (2016.01) | |
| A23G 3/42 | (2006.01) | |
| A61K 36/88 | (2006.01) | |
| C13B 40/00 | (2011.01) | |
| A23G 3/48 | (2006.01) | |
| A61K 47/26 | (2006.01) | |
| B65B 63/08 | (2006.01) | |
| C13K 1/00 | (2006.01) | |
| C13K 11/00 | (2006.01) | |
| A23L 29/30 | (2016.01) | |
| A23L 33/125 | (2016.01) | |

(52) U.S. Cl.
CPC ............... *C13B 50/00* (2013.01); *A23G 3/42* (2013.01); *A23G 3/48* (2013.01); *A23L 5/00* (2016.08); *A23L 29/30* (2016.08); *A61K 36/88* (2013.01); *A61K 47/26* (2013.01); *B65B 63/08* (2013.01); *C13B 40/007* (2013.01); *C13B 50/002* (2013.01); *C13K 1/00* (2013.01); *C13K 11/00* (2013.01); *A23L 33/125* (2016.08); *A23V 2002/00* (2013.01)

(58) Field of Classification Search
None
See application file for complete search history.

(56) References Cited

U.S. PATENT DOCUMENTS

| | | |
|---|---|---|
| 3,928,121 A | 12/1975 | Zepeda-Castillo |
| 7,763,570 B1 | 7/2010 | Rayborn et al. |
| 2008/0248176 A1 | 10/2008 | Brown |
| 2008/0248183 A1 | 10/2008 | Brown |
| 2008/0268109 A1 | 10/2008 | Roman et al. ............... 426/231 |
| 2009/0029009 A1 | 1/2009 | St. Phard et al. |
| 2009/0029010 A1 | 1/2009 | Dince |
| 2009/0148580 A1 | 6/2009 | Heyer et al. |
| 2009/0226575 A1* | 9/2009 | Roman .................... A23L 27/34 426/231 |
| 2009/0311370 A1 | 12/2009 | Ogura et al. ................ 426/13 |
| 2011/0052755 A1* | 3/2011 | Fiorenza ................... A23G 1/48 426/3 |
| 2012/0034309 A1 | 2/2012 | Rowe |
| 2014/0079801 A1 | 3/2014 | Rowe |
| 2014/0112997 A1 | 4/2014 | Rowe |

FOREIGN PATENT DOCUMENTS

| | | |
|---|---|---|
| WO | WO 02/066517 | 8/2002 |
| WO | WO 2007/142306 | 12/2007 |
| WO | 2010/081232 A1 | 7/2010 |
| WO | WO 2012/149069 | 11/2012 |

* cited by examiner

*Primary Examiner* — Christopher R Tate
*Assistant Examiner* — Randall Winston
(74) *Attorney, Agent, or Firm* — Norton Rose Fulbright US LLP

(57) ABSTRACT

The present invention relates to a *agave* syrup product having a low water content. The *agave* syrup product retains the physical and palatable properties of untreated *agave* syrup while having a prolonged shelf-life. It can be advantageously used to sweeten beverages (such as hot beverages) and in the manufacture of pharmaceutical compositions (such as throat lozenges) and/or confectionary.

11 Claims, No Drawings

SOLID AGAVE SYRUP COMPOSITIONS

CROSS-REFERENCE TO RELATED APPLICATION

This application is a national phase application under 35 U.S.C. § 371 of International Application No. PCT/CA2013/050538 filed Jul. 11, 2013, which claims priority from U.S. provisional application Ser. No. 61/671,159 filed on Jul. 13, 2012. The entire contents of each of the above-referenced disclosures is specifically incorporated by reference herein without disclaimer.

FIELD OF THE INVENTION

This invention relates to solid *agave* syrup products having a low water content. The organoleptic and physical characteristics of the *agave* syrup product are very similar to those of the original liquid *agave* syrup. In addition, the sugars in the *agave* syrup product are not crystallized.

BACKGROUND

*Agave* syrup (also called *agave* nectar) is a sweetener which can be obtained from several species of *agave*, including the blue *agave* (*Agave tequilana*), salmiana *agave* (*agave salmiana*), green *agave*, grey *agave*, thorny *agave* and rainbow *agave*. *Agave* syrup is sweeter than honey, though less viscous.

To produce *agave* syrup from the *Agave tequiliana* plant, juice is expressed from the core of the *agave*, called the piña. The juice is filtered, then heated to hydrolyze polysaccharides into simple sugars. The main polysaccharide of the *agave* juice is called inulin or fructosan and comprises mostly fructose units. The *agave* juice also contains glucose. The filtered, hydrolyzed juice is concentrated to a syrupy liquid, slightly thinner than honey, from light- to dark-amber depending on the degree of processing.

*Agave salimiana* is processed differently than *Agave tequiliana*. As the plant gestates, it starts to grow a stalk called a quiote. The stalk is cut off before it fully grows, creating a hole in the center of the plant that fills with a liquid called aguamiel. The liquid is collected daily and the fructans hydrolysed by enzymes into fructose and dextrose.

Alternative methods used to process the *agave* juice without heat, include, but are not limited to acid hydrolysis, enzymatic treatment (for example with enzymes derived from *Aspergillus niger*) as well as filtration (such as ultra-filtration).

An inulin syrup, which may be obtained from *agave* plants, can be processed into fructose syrup for use in foods and beverages. The conventional techniques for producing fructose syrup from *agave* plants produce syrups of differing quality, depending on the particular technique. High quality fructose syrup is clear in color and substantially free of the taste and aroma of the *agave* plant. A poor quality fructose syrup has a yellow-brownish color and is tainted by the taste and smell of the *agave* plant.

*Agave* syrups consists primarily of fructose and glucose. Depending on the source, the fructose content can vary between 56% and 92% whereas the glucose content can vary between 8% and 20%. One of *agave* syrup's principal advantage is that its glycemic index and glycemic load are comparable to fructose, which in turn has a much lower glycemic index and glycemic load than sucrose. Further, *agave* syrup is 1.4 to 1.6 times sweeter than sucrose. *Agave* syrup is often substituted for sugar or honey in recipes. *Agave* syrup dissolves quickly, it can be advantageously used as a sweetener for cold beverages.

Since the applications and shelf-life of liquid *agave* are limited, it would be highly desirable to be provided with an *agave* syrup processed into a solid form and therefore having a low water content. It is preferred that the *agave* syrup product possesses the distinctive taste and color of the original liquid *agave* syrup. Preferably, the *agave* syrup product would not contain any additive(s). It would nevertheless be preferably a very versatile product that could be processed into various food, nutraceutical, dietary supplement or natural health product applications.

SUMMARY

The present invention relates to an *agave* syrup product having a low water content. In an embodiment, the *agave* syrup product is a pure dehydrated solid *agave* syrup product.

According to a first embodiment, the present invention provides a solid *agave* syrup product consisting essentially of *agave* syrup and having a moisture content equal to or less than about 0.05% (w/w). As used herein, the term "consisting essentially of" indicates that the *agave* syrup product is composed of *agave* syrup and its usual constituents (refer to the definition of *agave* syrup below) and that no further additives are required to generate the dehydrated product or to store it. The present invention also provides an *agave* syrup product consisting of *agave* syrup and having a moisture content equal to or less than about 0.5% (w/w), about 0.4%, about 0.3%, about 0.2%, about 0.1%, about 0.09%, about 0.08%, about 0.07%, about 0.06%, about 0.05%, about 0.04%, about 0.03%, about 0.02% or about 0.01%. In a further embodiment, the moisture content of the *agave* syrup product is equal to but not higher than about 0.5% (w/w), than about 0.4%, than about 0.3%, than about 0.2%, than about 0.1%, than about 0.09%, than about 0.08%, than about 0.07%, than about 0.06%, than about 0.05%, than about 0.04%, than about 0.03%, than about 0.02% or than about 0.01%. In some embodiment, the solid *agave* product can be obtained by submitting the *agave* syrup to a raise in temperature (from room temperature to 90° C. for example) as well to a partial vacuum (for example 28 inches of Hg) for a certain period of time (70 minutes for example). In additional embodiments, the sugars of the solid *agave* products are not crystallized (e.g. they are in an uncrystallized form). In a further embodiment, the solid *agave* product is translucent and its color is similar to the color of the untreated *agave* syrup. In further embodiment, the solid *agave* product can be further processed once it has set into a solid (cut, crushed or powdered for example). In yet another embodiment, the solid *agave* product can be used as a sweetener. In still another embodiment, the *agave* syrup product or the processed *agave* syrup can be wrapped in a water-impermeable package. In this particular embodiment, the *agave* syrup product, when placed into a water impermeable packaging, can have a storage time of three years (or more) without substantially reabsorbing water.

According to a second embodiment, the present invention also provides an *agave* composition comprising the solid *agave* product described herein and at least one additive. In an embodiment, the additive is incorporated to an *agave* syrup which already has been dehydrated and is not included in the *agave* syrup prior to dehydration. Various additives can be added to the *agave* syrup product but they should not materially affect the characteristics of the product (such as its moisture content). In some embodiments, the additive can be a flavor, such as, for example, a spearmint, a eucalyptus, a menthol and/or a lemon flavor. In other embodiment, the at least one additive is a preservative (such as, for example, a sugar alcohol). In another embodiment, the *agave* composition can be a confectionary. In a further embodiment, the *agave* composition can be a pharmaceutical composition (such as, for example a throat lozenge).

DETAILED DESCRIPTION OF VARIOUS EMBODIMENTS

In accordance with the present invention, there is provided a solid *agave* syrup product having a moisture content equal to or less than 0.05%. The *agave* syrup product described herein consists essentially of a liquid *agave* syrup to which water has been removed. It is pure *agave* syrup product to which no additive has been added during the dehydration process. The *agave* syrup product is not limited to any specific manufacturing technique. However, since the *agave* syrup product retains the color, characteristics and the taste of untreated *agave* syrup, care must be taken in selecting an appropriate manufacturing technique that will preserve the original *agave* syrup color, characteristics and taste.

The present invention provides a solid *agave* syrup product consisting essentially of *agave* syrup. In a further embodiment, the *agave* syrup product consists of *agave* syrup. As used herein, the term "*agave* syrup" is referred to as a processed juice obtained from the *agave* sp. plant (e.g. also referred to as processed sap or processed aguamiel). Such processing can be, for example, a heat treatment, a pH treatment (such as an acid treatment), an enzymatic treatment and/or a fermentation. Such process may be useful in breaking down the polysaccharides (e.g. inulin) in the *agave* juice, remove impurities, etc. The chemical composition of *agave* syrup varies depending on syrup source, season and production methods. Storage conditions may also influence final composition, with the proportion of disaccharides increasing over time. Processed *agave* syrup contains both fructose and glucose, however, it is usually considered that the proportion of fructose is higher than the proportion of glucose. Processed *agave* syrup also contains lesser amounts of inulin, other disaccharides and oligosaccharides (such as mannitol). In an embodiment, the *agave* syrup comprises between 50% and 90% of fructose, between 5% to 45% glucose and the remaining constituents including inulin. The moisture content of *agave* syrup is usually at least 20% and usually no more than 30%.

In the context of the present invention, the term "*agave* syrup" excludes the sap obtained from the *agave* plant. Further, in some embodiments, besides the enzymatic break down of inulin, an appropriate source processed *agave* syrup has not been enriched by or depleted from a specific species of polysaccharide, especially compositions enriched in inulin. For example, inulin-enriched liquid compositions (such as inulin syrup for example) from *agave* sap and/or syrup are not considered to an appropriate source *agave* syrup.

The liquid *agave* syrup that can be used in the products and compositions described herein can be semi-processed (such as strained or filtered *agave* syrup) or fully processed (e.g. heat- and/or acid-treated). The *agave* syrup product can be made with liquid *agave* syrup originating from any *agave* source. Known *agave* sources include, but are not limited to, *Agave americana*, *Agave angustifolia*, *Agave tequilana*, and *Agave attenuata*. The liquid *agave* syrup used to manufacture the *agave* syrup product can be derived from a single *Agave* sp. source or from a combination of *agave* sp. sources depending on the desired properties of the final product.

Once the processed *agave* syrup has been provided, it is further processed in order to reduce its moisture content to at least about 0.5% and provide an *agave* syrup in a solid dehydrated form. As used herein "solid *agave* syrup product" refers to a substance derived from *agave* syrup that is not liquid and that can be used as a source of nourishment. The *agave* syrup product can be easily handled (e.g. deposited in a mold) because it is not tacky or soft. In some embodiment, the *agave* syrup product is hyaline. In another embodiment, the *agave* syrup product is not initially processed as powder. As it will be shown below in the Example section, a dehydrated *agave* syrup product containing more than 0.5% w/w of water (and in embodiments, more than about 0.05% w/w of water) does not settle in a solid form once it has been cooled at room temperature. As such, because the *agave* syrup product described herein has a moisture content lower than about 0.5% w/w (and in embodiments, no more than about 0.5%), it is not tacky or sticky and can be easily be handled without substantially transferring to the surface manipulating the product (such as the skin or the package).

In yet another embodiment, the *agave* syrup product described herein is a pure and/or dried *agave* syrup product. As used herein, the term "pure" *agave* syrup product refers to a product that is free or substantially free from exogenous additives (such as for example exogenous polysaccharide (polyol, sucrose, stevia or high-fructose corn syrup)) with respect to the original liquid *agave* syrup. On the other hand, a "dried" or "dehydrated" *agave* syrup product refers to the fact that the moisture content is limited to no more than about 0.5% w/w, about 0.4% w/w, about 0.3% w/w, about 0.2% w/w, about 0.1% w/w, about 0.09% w/w, about 0.08% w/w, about 0.07% w/w, about 0.06% w/w, about 0.05% w/w, about 0.04% w/w, about 0.03% w/w, about 0.02% w/w or about 0.01% w/w.

The person skilled in the art can easily assess the percentage of moisture in a *agave* syrup product using methods readily known in the art. The moisture content of a food product is usually defined through the following formula:

$$\% \text{ moisture} = (m_w/m_{sample}) \times 100$$

In this formula, $m_w$ is the mass of the water and $m_{sample}$ is the mass of the sample. The mass of water is related to the number of water molecules ($n_w$) by the following expression:

$$M_w = n_w M_w/N_A,$$

In this formula, $M_w$ is the molecular weight of water (18.0 g per mole) and $N_A$ is Avodagro's number ($6.02 \times 10^{23}$ molecules per mole). In principle, the moisture content of a *agave* syrup product can therefore be determined accurately by measuring the number or mass of water molecules present in a known mass of sample. When determining the moisture content of a food it is important to prevent any loss or gain of water. For this reason, exposure of a sample to the normal atmosphere, ambient temperature and excessive temperature fluctuations, should be minimized.

In one embodiment, a spectroscopic method can be used to determine the moisture content of the *agave* syrup product. Spectroscopic methods utilize the interaction of electromagnetic radiation with materials to obtain information about their composition, e.g., X-rays, UV-visible, NMR, microwaves and infra-red (IR). The spectroscopic methods developed to measure the moisture content of foods are based on the fact that water absorbs electromagnetic radiation at characteristic wavelengths that are different from the other components in the food matrix. Microwave and infrared radiation are absorbed by materials due to their ability to promote the vibration and/or rotation of molecules. The analysis is carried out at a wavelength where the water molecules absorb radiation, but none of the other components in the food matrix do. A measurement of the absorption of radiation at this wavelength can then be used to determine the moisture content: the higher the moisture content, the greater the absorption. Instruments based on this principle are commercially available and can be used to determine the moisture content in a few minutes or less.

In another embodiment, a chemical reaction, such as a colometric reaction, can be used for the determination of moisture in the *agave* syrup product. The Karl Fischer titration is often used for determining the moisture content of foods that have low water contents (e.g. dried fruits and vegetables, confectionery, coffee, oils and fats). It is based on the following reaction:

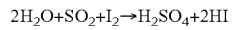

$$2H_2O + SO_2 + I_2 \rightarrow H_2SO_4 + 2HI$$

This reaction was originally used because HI is colorless, whereas $I_2$ is a dark reddish brown color, hence there is a measurable change in color when water reacts with the added chemical reagents. Sulfur dioxide and iodine are gaseous and would normally be lost from solution. For this reason, the above reaction has been modified by adding solvents (e.g., $C_5H_5N$) that keep the $S_2O$ and $I_2$ in solution, although the basic principles of the method are the same. The food to be analyzed is usually placed in a beaker containing solvent and is then titrated with Karl Fischer reagent (a solution that contains iodine). While any water remains in the sample the iodine reacts with it and the solution remains colorless (HI), but once all the water has been used up any additional iodine is observed as a dark red brown color ($I_2$). The volume of iodine solution required to titrate the water is measured and can be related to the moisture content using a pre-prepared calibration curve. The precision of the technique can be improved by using electrical methods to follow the end-point of the reaction, rather than observing a color change.

One particular advantage of the solid *agave* syrup product described herein is that, during its dehydration process, no additives are being added to facilitate water removal, to stabilize the resulting dehydrated product or to limit the adhesion of the product to its packaging membrane.

When the *agave* syrup product is wrapped in a water-impermeable package, its storage time is of about three years or even more (depending on the WVTR of the package). During storage, the product does not substantially reabsorb water and as such its water content is substantially constant. As used herein, an *agave* syrup product that does not "substantially" reabsorb water is a *agave* syrup product that possesses a water content of less than about 0.5% w/w during its storage. As indicated above, when the water content of the *agave* syrup product exceeds 0.5% w/w, the *agave* syrup product becomes tacky.

Another advantage of the solid *agave* syrup product described herein is that the majority of the sugars present are in an uncrystallized form. As used herein the term "uncrystallized" refer to the absence of sugar crystals that can be felt in the mouth and/or visible to the naked eye. The *agave* syrup product has a smooth texture and does not contain granulated *agave* syrup crystals which can be seen by the naked eye or be felt in the mouth.

A further advantage of the *agave* syrup product described herein is that, once cooled at room temperature after dehydration (but prior to other processing steps), it is a translucent product having the color characteristics of the original *agave* syrup (e.g. translucent/transparent/clear or, in some embodiments, presenting shades of yellow and/or brown). However, upon water removal, it is assumed that the solid *agave* syrup product will have an increase in color intensity that the shade of product could be perceived as different (e.g. darker) than in the liquid *agave* syrup.

Another advantage of the *agave* syrup product described herein is that, once cooled at room temperature after vacuum dehydration (but prior to other processing steps) it has the organoleptic properties of the original *agave* syrup (flavor, intensity, mouth feel), e.g. a distinct *agave* flavor. However, upon water removal, it is assumed that the solid *agave* syrup product will have an increase in flavor intensity and stickiness and that the sweetness level of product could be perceived as different (e.g. heightened) than in the liquid *agave* syrup.

As indicated above, the solid *agave* syrup product is not limited to a specific manufacturing technique. In one advantageous embodiment and as shown below, the liquid *agave* syrup is submitted to vacuum drying to lower its water content and generate the *agave* syrup product. During the dehydration process, the liquid *agave* syrup is not supplemented with an exogenous source of additive (such as for example, a polysaccharide selected from the group consisting of polyol, sucrose and high-fructose corn syrup). The time, temperature and pressure variables used should be designed to generate a solid *agave* syrup product having similar organoleptic characteristics as the original liquid (e.g. hydrated) *agave* syrup. In an embodiment, the liquid *agave* syrup can be heated from ambient temperature of less than 98° C. (e.g. 97° C., 96° C., 95° C., 94° C., 93° C., 92° C., 91° C. or 90° C. for example). While the temperature is gradually increased, a pressure of at least 26 inHg (27 ing or 28 inHg for example) is applied to the liquid *agave* syrup. This vacuum is maintained until the moisture content reaches a specific threshold (for example less than 0.5%, 0.4%, 0.3%, 0.2%, 0.1%, 0.09%, 0.08%, 0.07%, 0.06%, 0.05%, 0.04%, 0.03%, 0.02% or 0.01%), depending on the final application of the product. The dehydration process for the production of the solid *agave* syrup product can last at least 60 minutes, at least 70 minutes, at least 80 minutes, at least 90 minutes, at least 100 minutes, at least 110 minutes or at least 120 minutes. The dehydration process is preferably conducted under constant stirring (or any other techniques known in the art) to evenly distribute the temperature in the *agave* syrup that is being dehydrated and/or to avoid burning of the *agave* syrup. As it is known in the art, the temperature, vacuum and time parameters can be modified to reach the desired temperature. These parameters will also depend on the amount of liquid *agave* syrup that is being processed as well as the content of original the liquid *agave* syrup (such as its moisture content).

Once the solid *agave* syrup product has been dehydrated (e.g. reached its moisture content equal to or less than 0.5%), it can be deposited into molds and cooled at room temperature. In some embodiments, the dehydrated *agave* syrup product is deposited into molds. The deposition into mold is preferably performed when the dehydrated *agave* syrup is at a temperature higher than the temperature it sets into a solid, for example, above 60° C. (and, in an embodiment, up to 90° C.). It should be noted that the dehydrated *agave* syrup (even at temperature higher than the temperature it sets into a solid) cannot be extruded as it is too soft to sustain such process. The cooled solid *agave* syrup product can be manufactured to any size that is convenient for the end-use, for example in formats ranging from μg to kg.

Optionally, the solid *agave* product can be packaged. Because of the hygroscopic nature of the dehydrated *agave* syrup product, it will tend to reabsorb water if it is not placed in a water impermeable package. For example, and depending on the relative humidity of the environment, if the product is left at ambient temperature, within a couple of days, it can become tacky and, within a couple of weeks, it can to become sticky. As such, in order to prolong the shelf life of the product, it can be packaged in a water-impermeable membrane. As used herein, a "water-impermeable package" or "water-impermeable membrane" refers to a material that limits the transmission of water vapor. In an embodiment, the water vapor transmission rate (WVTR) of the "water-impermeable" package or membrane is below 0.1 gm/100 in$^2$ or below about 0.01 gm/100 in$^2$. Because the *agave* syrup product is mainly used as a food or as a food additive, the package can be of food or pharmaceutical grade. Further, since the package can optionally be submitted to heat to seal it around the *agave* syrup product, the package or membrane can also be resistant to heat.

Once the *agave* product has been dehydrated, it can optionally be further processed into an *agave* composition. For example, in an embodiment, it is contemplated that a flavor can be added to the solid *agave* syrup product described after it has been dehydrated (but prior to the product setting into a solid). The added flavor may be, for example, a sweet or a savory flavor. Sweet flavors include, but are not limited to fruits (peach, pear, apple), citrus (orange, lemon, lime), berry (raspberry, strawberry, blueberry), spice (vanilla, cinnamon, clove, lavender), caramel, butterscotch, maple, mint (spearmint, menthol). Savory flavors include, but are not limited to, ginger, pepper (black, white, pink, green, hot), etc. Other flavors, such as coffee, tea, herbal tea and/or alcohol, can also be added. In an embodiment, the flavor can be derived from an oil, a powder or an extract (such as, for example, an alcohol extract). In one preferred embodiment, the solid *agave* product is combined with a menthol and a eucalyptus flavor.

In other optional or complementary embodiments, a preservative can be added to the dehydrated *agave* product (after its dehydration) to prolong its self-life, delay or limit water reabsorption and/or preserve the formation of crystals. Such preservative can be an emulsifier, an anti-sticking agent and/or a stabilizer, including, but not limited to bee wax, carnauba wax, a sugar (such as trehalose and/or sucrose), a sugar alcohol or polyol (such as, for example, methanol, ethylene glycol, glycerol, erythritol, threitol, arabitol, ribitol, xylitol, mannitol, sorbitol, galactitol, iditol, volemitol, fucitol, inositol, maltitol, lactitol, isomalt, maltotriitol, maltotetraitol and/or polyglycitol) and/or other food/pharmaceutical processing aids. In one exemplary embodiment, the solid *agave* syrup product (optionally previously crushed or powdered) is admixed with a processing aid (for example a sugar alcohol) for delivering a therapeutic product.

In other optional or complementary embodiments, a preservative can be added to the dehydrated *agave* syrup to prolong its self-life, delay or limit water reabsorption and/or preserve the formation of crystals. Such preservative can be an emulsifier, an anti-sticking agent and/or a stabilizer, including, but not limited to bee wax, carnauba wax, maltodextrin, dextrose or other food/pharmaceutical processing aids.

The solid *agave* product can be used without any further processing, mostly as a sweetener in food applications. However, the solid *agave* syrup product can be further processed for use in other food applications (such as confectionary, dessert topping and/or sweet ingredient), in natural products as well as in pharmaceutical applications (such as throat lozenges). In such instances, the solid *agave* syrup product can be further powdered, crushed, ground and/or granulated for these additional applications.

Particles can thus be made from the solid *agave* syrup product and used in various applications. For example, when a coarser particle is required, the solid *agave* syrup can be processed into a "granular" form particles having a size distribution that ranges between about 0.25 and 2 mm. On the other hand, when a finer particle is needed, the solid *agave* syrup product can be processed into a "powder" form particles having a size distribution that ranges between 62.5 to 125 μm. The size distribution of the particles can be assessed by the techniques known in the art, such as the Gates-Gaudin-Schuhmann method, the Rosin-Rammler method, the modified Gaudin-Meloy method, the Log-normal method and/or the modified beta method. Similar to what has been indicated above for the solid *agave* syrup products, the particles of the solid *agave* syrup can also be packaged in a water-impermeable membrane to slow down, delay or prevent water reabsorption.

The *agave* syrup product or the *agave* composition as described herein can be advantageously used to sweeten a beverage. When the solid *agave* syrup product is placed in an aqueous-based beverage, it reabsorbs water and dissolves to sweeten the beverage. The application of the *agave* syrup product is not limited to a specific type of beverage or to beverages having a specific temperature.

Because of the excellent palatable properties of the solid *agave* syrup, the *agave* syrup product or the *agave* composition described herein can be further processed into a confectionery. In order to introduce the solid *agave* syrup product into a confectionery, and as indicated above, it can be physically processed (crushed, powdered, coated in a solution) and/or flavors can be added. Alternatively or concomitantly, the manufacturing process of the product can also be altered to introduce additional components of the confectionery.

Further, the solid *agave* syrup can be formulated into a pharmaceutical composition to improve its taste (e.g. providing a sweet taste), without influencing too much the glycemic index of the composition. Such *agave*-based pharmaceutical composition can be especially useful for designing pharmaceutical formulations for individuals suffering from diabetes.

The present invention will be more readily understood by referring to the following examples which are given to illustrate the invention rather than to limit its scope.

Example I—Production of Solid *Agave* Syrup Product

The ingredient used in the following protocols is 100% *agave* syrup. The initial moisture content of *agave* is between 22 to 26%. The *agave* syrup is poured into a reactor vessel and a vacuum of 26 to 28 inches of Hg was applied. The time and temperatures applied are presented in the protocols. The *agave* syrup is stirred with a rotating paddle throughout process at a constant rate of 30 rpm. Prior to dispensing the evaporated *agave* syrup product in the molding trays, an aliquot was removed to determine the moisture content using and infra-red moisture meter in order to rapidly assess the moisture content. The evaporated *agave* syrup was then deposited into molding trays and cooled to room temperature.

Protocol A.

The *agave* syrup was submitted to a vacuum dehydration at a temperature of 98° C., under a vacuum of 28 inches of Hg (at T=0), as provided in Table A. After 60 minutes, the vacuum was released and the product was poured into molds. During the process, flash boiling was observed as soon as constant vacuum applied. Vacuum was released and reapplied in order to keep the *agave* syrup from entering the vacuum tubing. The final product obtained did not set into a solid after cooling. The moisture content of the end product, as measured with an infra-red-meter, was determined to be greater than 2.0% (w/w).

TABLE A

Time and temperature parameters of protocol A.

| Time (minutes) | Temperature (° C.) |
| --- | --- |
| 0 | 45 |
| 5 | 50 |
| 10 | 55 |
| 15 | 60 |
| 20 | 65 |
| 25 | 70 |
| 30 | 75 |
| 35 | 80 |
| 40 | 85 |
| 45 | 90 |
| 50 | 95 |
| 55 | 98 |
| 60 | 98 |

Protocol B.

The *agave* syrup was submitted to a vacuum dehydration at a temperature of 98° C., under a vacuum of 28 inches of Hg (at T=0), as provided in Table B. After 80 minutes, the vacuum was released and the product was poured into molds. During the process, flash boiling was observed as soon as a temperature of 40° C. was reached. Vacuum was released and reapplied in order to keep the *agave* syrup from entering the vacuum tubing. The final product obtained did not set into a solid after cooling. The moisture content of the end product, as measured with an infra-red moisture meter, was determined to be greater than 1.18% (w/w).

TABLE B

Time and temperature parameters of protocol B.

| Time (Minutes) | Temperature (° C.) |
| --- | --- |
| 0 | 30 |
| 5 | 35 |
| 10 | 40 |
| 15 | 45 |
| 20 | 50 |
| 25 | 55 |
| 30 | 60 |
| 35 | 65 |
| 40 | 70 |
| 45 | 75 |
| 55 | 80 |
| 60 | 85 |
| 65 | 90 |
| 70 | 95 |
| 75 | 98 |
| 80 | 98 |

Protocol C.

The *agave* syrup was submitted to a vacuum dehydration at a temperature of 90° C., under a vacuum of 28 inches of Hg (at T=0), as provided in Table C. After 110 minutes, the vacuum was released and the product was poured into molds. No flash boiling was observed during the process. Fluidity of final product (at temperatures between 60 and 90° C.) after dehydration was appropriate for depositing into moulds. The final product obtained did set into a solid after cooling and had a translucent appearance. The moisture content of the end product, as measured with an infra-red moisture meter, was determined to be greater less than 0.05% (w/w).

TABLE C

Time and temperature parameters of protocol C.

| Time (minutes) | Temperature (° C.) |
| --- | --- |
| 0 | 30 |
| 5 | 30 |
| 10 | 35 |
| 15 | 35 |
| 20 | 35 |
| 25 | 35 |
| 30 | 40 |
| 35 | 40 |
| 40 | 40 |
| 45 | 45 |
| 50 | 50 |
| 55 | 55 |
| 60 | 60 |
| 65 | 65 |
| 70 | 70 |
| 75 | 75 |
| 80 | 80 |
| 85 | 85 |
| 90 | 90 |
| 95 | 90 |
| 100 | 90 |
| 105 | 90 |
| 110 | 90 |

Protocol D.

The *agave* syrup was submitted to a vacuum dehydration at a temperature of 90° C., under a vacuum of 28 inches of Hg (at T=0), as provided in Table D. After 85 minutes, the vacuum was released and the product was poured into molds. No flash boiling was observed during the process. Fluidity of final product (at temperatures between 60 and 90° C.) after dehydration was appropriate for depositing into moulds. The final product obtained did set into a solid after cooling and had a translucent appearance. The moisture content of the end product, as measured with an infra-red-meter, was determined to be greater less than 0.05% (w/w).

TABLE D

Time and temperature parameters of protocol D.

| Time (minutes) | Temperature (° C.) |
| --- | --- |
| 0 | 35 |
| 5 | 35 |
| 10 | 35 |
| 15 | 35 |
| 20 | 40 |
| 25 | 40 |
| 30 | 45 |
| 35 | 50 |
| 40 | 55 |
| 45 | 60 |
| 50 | 65 |
| 55 | 70 |

TABLE D-continued

Time and temperature parameters of protocol D.

| Time (minutes) | Temperature (° C.) |
| --- | --- |
| 60 | 75 |
| 65 | 8 |
| 70 | 85 |
| 75 | 90 |
| 80 | 90 |
| 85 | 90 |

Protocol E.

The *agave* syrup was submitted to a vacuum dehydration at a temperature of 90° C., under a vacuum of 28 inches of Hg (at T=0), as provided in Table E. After 70 minutes, the vacuum was released and the product was poured into molds. No flash boiling was observed during the process. Fluidity of final product (at temperatures between 60 and 90° C.) after dehydration was appropriate for depositing into moulds. The final product obtained did set into a solid after cooling and had a translucent appearance. The moisture content of the end product, as measured with an infra-red-meter, was determined to be less than 0.05% (w/w).

TABLE E

Time and temperature parameters of protocol E.

| Time (minutes) | Temperature (° C.) |
| --- | --- |
| 0 | 35 |
| 5 | 40 |
| 10 | 40 |
| 15 | 40 |
| 20 | 40 |
| 25 | 42 |
| 30 | 42 |
| 35 | 45 |
| 40 | 45 |
| 45 | 50 |
| 50 | 60 |
| 55 | 70 |
| 60 | 80 |
| 65 | 90 |
| 70 | 90 |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A solid *agave* syrup product consisting essentially of an *agave* syrup having a moisture content equal to or less than about 0.5% (w/w).

2. The solid *agave* syrup product of claim 1, wherein the moisture content is equal to or less than about 0.3%.

3. The solid *agave* syrup product of claim 1, wherein the moisture content is equal to or less then about 0.1%.

4. The solid *agave* syrup product of claim 1, wherein the moisture content is equal to or less than about 0.05%.

5. The solid *agave* syrup product of claim 1, wherein the moisture content is equal to or less than about 0.01%.

6. The solid *agave* syrup product of claim 1, wherein the sugars of the solid *agave* syrup product are in an uncrystallized form.

7. The solid *agave* syrup product of claim 1, wherein the solid *agave* syrup product is translucent.

8. The solid *agave* syrup product of claim 1 produced by a process comprising submitting a liquid *agave* syrup to a vacuum of at least 28 inHg, to a raise in temperature from room temperature to 90° C. and for a period of time of at least 70 minutes to obtain a dehydrated *agave* syrup product.

9. The solid *agave* syrup product of claim 8, wherein the process further comprises cooling the dehydrated *agave* syrup product to room temperature.

10. The solid *agave* syrup product according to claim 9, wherein the process further comprises processing the solid *agave* syrup product in a powder.

11. The solid *agave* syrup product according to claim 8, wherein the process further comprises placing the solid *agave* syrup product in a water-impermeable package.

* * * * *